United States Patent
Nagamine et al.

(10) Patent No.: US 8,300,907 B2
(45) Date of Patent: Oct. 30, 2012

(54) COUCH POSITIONING SYSTEM FOR RADIOTHERAPY, TREATMENT PLAN UNIT, AND COUCH POSITIONING UNIT

(75) Inventors: Yoshihiko Nagamine, Hitachi (JP); Toshie Sasaki, Hitachi (JP); Takao Kidani, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 1064 days.

(21) Appl. No.: 12/018,537

(22) Filed: Jan. 23, 2008

(65) Prior Publication Data
US 2008/0232664 A1 Sep. 25, 2008

(30) Foreign Application Priority Data
Mar. 20, 2007 (JP) ................. 2007-072440

(51) Int. Cl.
*G06K 9/20* (2006.01)

(52) U.S. Cl. ........ 382/128; 382/276; 128/920; 128/922; 128/923; 600/1; 600/2; 607/1; 607/2; 607/3; 607/80

(58) Field of Classification Search .............. 382/128, 382/131, 132, 276, 285; 128/920, 922, 923; 600/1, 2; 607/1, 2, 3, 80
See application file for complete search history.

(56) References Cited

U.S. PATENT DOCUMENTS

| 5,117,829 | A | 6/1992 | Miller et al. | |
|---|---|---|---|---|
| 5,825,845 | A | 10/1998 | Blair et al. | |
| 2005/0228255 | A1* | 10/2005 | Saracen et al. | 600/407 |
| 2007/0003123 | A1* | 1/2007 | Fu et al. | 382/131 |
| 2008/0317203 | A1* | 12/2008 | Ferrand et al. | 378/65 |
| 2009/0123042 | A1* | 5/2009 | Gagnon et al. | 382/128 |

FOREIGN PATENT DOCUMENTS

| EP | 1683545 | 7/2006 |
|---|---|---|
| JP | 4-295339 A | 10/1992 |
| JP | 2000-510023 A | 8/2000 |
| WO | 98/18523 | 5/1998 |

* cited by examiner

*Primary Examiner* — David A Vanore
*Assistant Examiner* — Nicole Ippolito
(74) *Attorney, Agent, or Firm* — Mattingly & Malur, PC

(57) ABSTRACT

An object of the present invention is to easily maintain the couch positioning accuracy and reduce the couch positioning time while resolving the complexity of input operations by the operator at the time of couch positioning. To accomplish the above object, calculation points are set to a CT image at the time of treatment planning, and the 3D coordinates of the set calculation point are set to a DRR image. When a couch positioning unit 115 loads the DRR image from an image server 109, it reads the coordinates of calculation points set to the DRR image and displays them on the monitor 116 together with the DRR image. Further, when DR image data is loaded into the couch positioning unit 115, the DR image is displayed on the monitor 116 and calculation points set to the DRR image are set also to the DR image.

17 Claims, 7 Drawing Sheets

COORDINATE SYSTEM OF VOXEL

CALCULATING COORDINATES
OF A CALCULATION POINT

FIG. 7

| No. | X | Y | Z |

DATA REPRESENTATION OF
A CALCULATION POINT

FIG. 8

| No. | X | Y |

DATA REPRESENTATION OF
A CALCULATION POINT

FIG. 9

| | | | | | | | | | | | | ADDITIONAL DATA AREA |
|---|---|---|---|---|---|---|---|---|---|---|---|---|
| ⟨3D POINT⟩ | No. | X | Y | Z | No. | X | Y | Z | No. | X | Y | Z |
| ⟨2D POINT⟩ | No. | X | Y | No. | X | Y | No. | X | Y | | | |
| ⟨IMAGE⟩ | VALUE | VALUE | VALUE | VALUE | VALUE | VALUE | | | | | | |

ADDING COORDINATES OF CALCULATION POINTS TO DRR IMAGE DATA

DRR AND DR IMAGE ARRANGEMENTS ON MONITOR

RECONSTRUCTING 3D COORDINATES
OF CALCULATION POINTS

COUCH POSITIONING SYSTEM FOR RADIOTHERAPY, TREATMENT PLAN UNIT, AND COUCH POSITIONING UNIT

BACKGROUND OF THE INVENTION

1. Field of the Invention

The present invention relates to a couch positioning system for radiotherapy which irradiates an irradiation target with various radiations, such as X-ray or proton beam and other particle beams, to perform treatment. The present invention also relates to a treatment plan unit and a couch positioning unit.

2. Description of the Related Art

Radiotherapy intended to necrose tumour cells by irradiating them with various radiations has been widely performed in recent years. Radiations presently used for treatment include not only the X-ray, which is most widely used, but also proton beam and other particle beams.

One of the important processes of radiotherapy is couch positioning. Couch positioning generally refers to a process comprising the steps of: comparing a DRR (Digital Reconstructed Radiograph) image outputted from a treatment plan unit with an X-ray image (Digital Radiograph image or DR image) taken with a patient lying down on a treatment bed (hereinafter abbreviated to couch) by use of an X-ray imaging unit before radiation irradiation, by a therapist or a doctor; calculating a gap between the position of an irradiation target determined by a treatment plan and the present position of the irradiation target on the couch; obtaining the couch displacement so that the two images are in alignment; and moving the couch.

The DRR image, a simulated X-ray image, is generated from an X-ray CT image taken at the time of treatment planning. At couch positioning, it may be possible to use an X-ray perspective image taken by use of an X-ray simulator as well as the above-mentioned DRR image as a reference image.

Examples of a typical method of couch positioning include a method of marking reference points (calculation points) on the DRR and DR images, which will be explained below.

In order to obtain the couch displacement, an operator uses a couch positioning unit having a function to display a DRR image and an X-ray image side by side. The couch positioning unit is composed of: monitors for image display; operation units which perform positioning operations; and input means such as a keyboard, a mouse, or the like.

The operator inputs calculation points by use of certain input means in such a way that calculation points overlap characteristic points in the DRR image reflected on the monitor of the couch positioning unit and markers (metallic pellets, etc.) existing within the irradiation target, the markers being embedded before CT imaging at the time of treatment planning and reflected also in the DRR image. The operator likewise inputs calculation points also in the DR image. After inputting of calculation points, calculation points in the DRR image and calculation points in the DR image are converted to coordinates having, for example, the image center as an origin. Converted coordinates are compared with each other to calculate the couch displacement. This kind of method is disclosed for example in JP-A-2000-510023. Further, since the DRR and DR images respectively taken from the irradiation direction and a direction perpendicular thereto are generally used, a total of four images are required.

SUMMARY OF THE INVENTION

With the conventional technique, calculation points are inputted to DRR and DR images at the time of couch positioning, i.e., immediately before irradiation of the irradiation target (calculation points are inputted to characteristic structures in the image and markers within the irradiation target reflected on the image). Therefore, the technique is complicated because of the necessity to input calculation points to two different images, and therefore requires great deal of attention to maintain the accuracy necessary for couch positioning. This has been a reason why couch positioning takes time.

Further, even at the time of second and subsequent couch positioning, calculation points are inputted to two different images (DRR and DR images) like the first couch positioning. Therefore, both the reproducibility of input coordinates of calculation points on the DRR image at first couch positioning and the reproducibility of input coordinates of calculation points on the DR image at first couch positioning depend on the skill of an operator who performs input operations. A great deal of effort has conventionally been required in order to maintain the positioning accuracy when couch positioning for the irradiation target is performed.

An object of the present invention is to provide a couch positioning system for radiotherapy which resolves the complexity of input operations that have been imposed on the operator at the time of couch positioning, making it easier to maintain the accuracy necessary for couch positioning, thereby shortening the couch positioning time.

Another object of the present invention is to provide a couch positioning system for radiotherapy which resolves the complexity of input operations that have been imposed on the operator at the time of second and subsequent couch positioning, thereby further improving the positioning accuracy through improved reproducibility of input coordinates of calculation points.

The above-mentioned problems are solved by a couch positioning system comprising: a first image file generator for operating and generating first image data for providing a first image, such as, for example, a reference image for couch positioning; adding the coordinates of set first calculation points to the first image data; and storing the first image data, thus generating a first image file; and providing a couch positioning unit for displaying the first image using the first image file; displaying the first calculation points at positions corresponding to the set first calculation points in the first image; displaying a second image which is the present image of an irradiation target on the couch; and generating couch positioning data by use of the coordinates of the first calculation points added to the first image data and the coordinates of second calculation points set to target positions in the second image.

The above-mentioned problems are also solved by the couch positioning unit comprising a second image file generator for generating new second image data reflecting the couch positioning data and coordinates of new second calculation points; adding the coordinates of the new second calculation points to the new second image data; and storing the new second image data, thus generating a second image file.

An essential reason for the above-mentioned problems is that calculation points are inputted to both DRR and DR images at the time of couch positioning. Therefore, there arise such problems as the reproducibility of input coordinates, complexity of input operations, and impossibility to shorten the positioning time.

In order to solve the above-mentioned problems, the present invention provides means for eliminating the need of inputting calculation points at the time of couch positioning to a first image (a DRR image generated from an X-ray CT image) to be used at the time of treatment planning.

Specifically, the first image file generator sets calculation points (first calculation points) to the X-ray CT image at the time of treatment planning, and sets 3D coordinates of the set calculation points to the DRR image (first image). When the couch positioning unit loads the DRR image from an image server, it reads the coordinates of calculation points set to the DRR image and then displays the DRR image as well as the calculation points (first calculation points) in the image on the monitor (display unit) of the couch positioning unit. Although the DRR image is a 2D image, calculation points are arranged in 3D space. When the second image (DR image) is taken and DR image data is loaded into the couch positioning unit, the couch positioning unit displays the DR image on the monitor. Preferably, calculation points set to the DRR image are also copied to the DR image. The operator of the couch positioning unit sets second calculation points by moving them to the target positions as second calculation points.

Thus, the operator can skip the process of inputting calculation points to the DRR image, making it possible to remarkably simplify the input process and resolve the complexity of input operations. Further, since it is only necessary for the operator to issue a calculation point correction command to the DR image, it becomes easier to maintain the couch positioning accuracy, i.e., calculation point accuracy, thereby shortening the couch positioning time.

Further, the use of the first image (DRR image) data having calculation point setup eliminates the need of inputting calculation points to two different images (DRR and DR images) even at the time of second and subsequent couch positioning. As a result, the same effects as those obtained at the time of first couch positioning can be obtained and also the reproducibility of input coordinates of calculation points improved, allowing further improvement of the positioning accuracy.

Further, when the couch positioning unit generates a second image file which stores second image data reflecting couch positioning data (displacement) and the coordinates of second calculation points, the same effects (reproducibility of input coordinates of calculation points and improvement in positioning accuracy) can be obtained by use of the second image data having second calculation point setup in the second image file instead of the first image (DRR image) data at the time of second and subsequent couch positioning.

Further, when a second image file which stores the second image data reflecting couch positioning data (displacement) and coordinates of second calculation points are generated, it is possible to easily and securely validate the couch positioning accuracy and status by use of data of the file after couch positioning.

In accordance with the present invention, the operator performing couch positioning can skip the process of inputting calculation points to the first image (DRR image), making it possible to remarkably simplify the input process and resolve the complexity of input operations. Further, since it is only necessary for the operator to issue a calculation point correction command to the second image (DR image), it becomes easier to maintain the couch positioning accuracy thereby shortening the couch positioning time.

Further, in accordance with the present invention, the use of the first image (DRR image) data having calculation point setup eliminates the need of inputting calculation points to two different images (DRR and DR images) even at the time of second and subsequent couch positioning. As a result, the same effects as those obtained at the time of first couch positioning can be obtained and also the reproducibility of input coordinates of calculation points improved, allowing further improvement of the positioning accuracy.

Further, in accordance with the present invention, the same effects (reproducibility of input coordinates of calculation points and improvement in positioning accuracy) can be obtained by use of the second image data having second calculation point setup in the second image file instead of the first image (DRR image) data at the time of second and subsequent couch positioning. Further, when a second image file is generated, it is possible to easily and securely validate the couch positioning accuracy and status by use of the file data after couch positioning.

BRIEF DESCRIPTION OF THE DRAWINGS

FIG. 7 is a diagram showing a data format of a calculation point.

FIG. 8 is a diagram showing a data format of a calculation point.

FIG. 9 is a diagram schematically showing a method of adding additional data, such as calculation points to DRR image data.

DESCRIPTION OF NUMERALS

Figure 1:
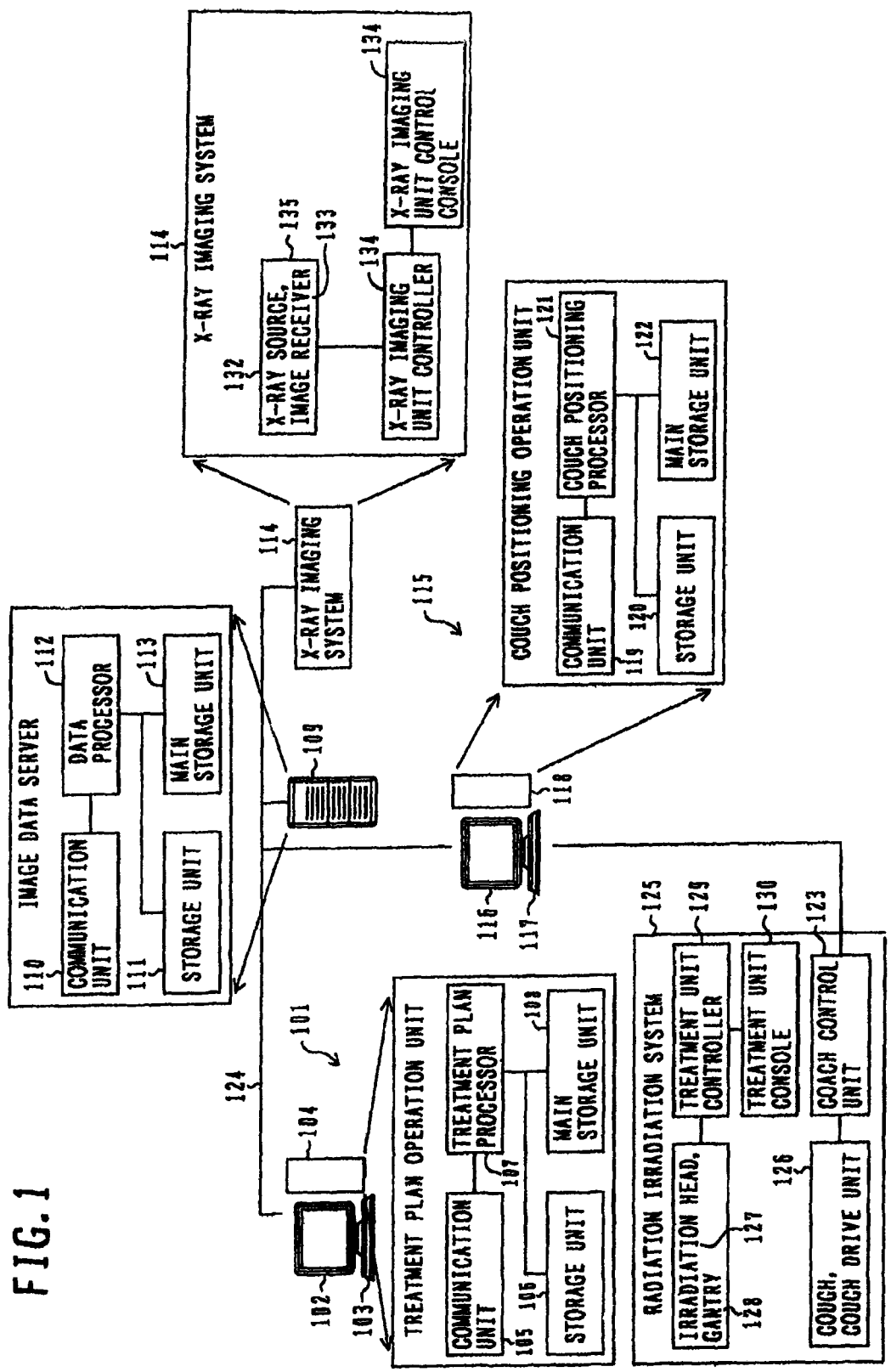
FIG. 1 is a diagram showing an overall configuration of a couch positioning system for radiotherapy according to an embodiment of the present invention.

101 . . . Treatment plan unit
102 . . . Monitor (first display unit)
103 . . . Input means
104 . . . Treatment plan operation unit (first image file generator)
105 . . . Communication unit
106 . . . Storage unit
107 . . . Treatment plan processor
108 . . . Main storage unit
109 . . . Image data server
110 . . . Communication unit
111 . . . Storage unit
112 . . . Data processor
113 . . . Main storage unit
114 . . . X-ray imaging system
115 . . . Couch positioning unit (including a second image file generator)
116 . . . Monitor (second display unit)
117 . . . Input means
118 . . . Couch positioning operation unit
119 . . . Communication unit
120 . . . Storage unit 121 ... Couch positioning processor
122 ... Main storage unit
123 ... Couch control unit
124 ... Network
125 ... Radiation irradiation system
126 ... Couch
127 ... Irradiation head
128 ... Gantry
129 ... Treatment unit controller
130 ... Treatment unit console
131 ... X-ray imaging unit control console
132 ... X-ray source
133 ... X-ray image receiver
134 ... X-ray imaging unit controller
135 ... X-ray imagining unit
701 ... First DRR image display area
702 ... Second DRR image display area
703 ... First DR image display area
704 ... Second DR image display area
705 ... Operation panel

DETAILED DESCRIPTION OF THE PREFERRED EMBODIMENTS

A preferred embodiment for carrying out the present invention will be explained in detail below with reference to the accompanying drawings.

System Configuration

FIG. 1 is a diagram showing an overall configuration of a couch positioning system for radiotherapy according to an embodiment of the present invention. First, each individual component of the system will be explained below with reference to FIG. 1.

The present system comprises a treatment plan unit 101, an image data server 109, a couch positioning unit 115, an X-ray imaging system 114, and a couch control unit 123.

The treatment plan unit 101, which provides a first file generator, is composed of: a treatment plan operation unit 104 which includes a device for operating a treatment plan; a monitor 102 (first display unit) which displays operation results of the treatment plan operation unit 104; and input means 103 for providing a command to the treatment plan operation unit 104 through a user interface displayed on the monitor 102. Generally, the input means 103 is a keyboard, a mouse, or the like. Further, graphical user interfaces (GUI) are frequently used as user interfaces.

The treatment plan operation unit 104 comprises: a communication unit 105 connecting with a network 124 to perform communication; a storage unit 106 which stores data, such as operation results and CT images, and a treatment plan program; a treatment plan processor 107 which controls operational processing of the treatment plan program and the treatment plan unit 101; and a main storage unit 108 which temporarily stores the treatment plan program stored in the storage unit 106 and data necessary for processing when the treatment plan program is operated by the treatment plan processor 107.

The image data server 109 is composed of: a communication unit 110 connecting with the network 124 to exchange data with other units; a storage unit 111 which stores data; a data processor 112 which controls each device in the image data server 109 to perform data operations such as data compression; and a main storage unit 113 which temporarily stores a processing program and process data used by the data processor 112.

The couch positioning unit 115 is composed of: a couch positioning operation unit 118 which performs couch positioning operations; a monitor 116 (second display unit) which displays operation results and user interfaces; and input means 117 for inputting a command to the couch positioning operation unit 118 and the couch control unit 123 through the user interfaces displayed on the monitor 116. A keyboard, a mouse, or the like is used as the input means 117. Further, the couch positioning operation unit 118 is composed of: a communication unit 119 which transmits input data and operation results; a storage unit 120 which stores data and the couch positioning operation program; a couch positioning processor 121 which performs couch positioning operations; and a main storage unit 122 which temporarily stores the operation program, input data, etc. for use by the couch positioning processor 121.

Although shown in a simplified manner, the couch control unit 123 is a control unit which controls a couch 126 on which an irradiation target (patient) subjected to radiation irradiation is placed. The couch control unit 123 receives a couch displacement calculated by the couch positioning unit 115 through operations and then transmits a move signal to a drive unit included in the couch 126. Although not described in detail in the present description, the couch 126 and the couch control unit 123 form a part of a radiation irradiation system 125. The radiation irradiation system 125 is composed of: an irradiation head (nozzle) 127 which irradiates radiation; a gantry 128 which supports the irradiation head 127; a treatment unit controller 129 which controls the irradiation head 127 and the gantry 128; and a treatment unit console 130 which provides a command to the treatment unit controller 129. Generally, the gantry 128 is provided with a rotational mechanism.

The X-ray imaging system 114 is composed of: an X-ray imaging unit 135 and an X-ray imaging unit control console 131. The X-ray imaging unit 135 is composed of: an X-ray source 132 and an X-ray image receiver 133 arranged at a position opposing to the X-ray source 132. The couch 126 is located between the X-ray source 132 and the X-ray image receiver 133, and an irradiation target is placed on the couch 126. The X-ray imaging unit 135 is used to image the irradiation target on the couch 126. Further, the X-ray image receiver 133 uses a flat panel detector, an image intensifier, or the like. The X-ray imaging unit control console 131 has a function to set the voltage of the X-ray source, imaging time, and other necessary imaging conditions to the X-ray imaging unit 135; and a function to transmit them to the X-ray imaging unit controller 134. The X-ray imaging unit controller 134 transmits a command received from the X-ray imaging unit control console 131 to the X-ray source 132 and the image receiver 133. Further, the X-ray imaging unit controller 134 has a function to receive an X-ray image taken by the X-ray imaging unit 135 from the X-ray imaging unit 135 and then transmit it to the image data server 109.

The treatment plan unit 101, the image data server 109, the couch positioning unit 115, the X-ray imaging system 114, and the couch control unit 123 are connected through the network 124, allowing data transmission and reception through the network.

Overview of Data Flow

Data flow in the system of FIG. 1 will be explained below with reference to FIG. 2. Data are generated by the treatment plan unit 101 and the X-ray imaging system 114, accumulated in the image data server 109, and used by the couch positioning unit 115.

Treatment Plan Unit 101

First, before irradiation of the irradiation target and couch positioning, a DRR image to be used for couch positioning is generated by use of the treatment plan unit 101. To accomplish this, the treatment plan unit 101 performs the steps of: loading CT image data for treatment planning from the image data server 109; storing the CT image in the storage unit 106 and the main storage unit 108 (Steps 201 and 202); setting calculation points (first calculation points or reference points) to markers and characteristic points displayed in the CT image (Step 203); generating a DRR image by use of the CT image with calculation point setup (Step 204); and transmitting the generated DRR image to the image data server 109 (Step 205). The image data server 109 stores the received DRR image in the storage unit 111 (Steps 206 and 207). Details of processing from Step 203 for setting calculation points to the CT image to Step 204 for generating a DRR image will be mentioned later.

X-Ray Imaging System 114

Before irradiation of the irradiation target, the X-ray imaging system 114 performs the steps of: taking an X-ray image of the irradiation target on the couch (Step 208) with the irradiation target placed on the couch; and transmitting the obtained X-ray data to the X-ray imaging unit control console 131 (Step 209). The X-ray imaging unit control console 131 performs the steps of: converting the X-ray data to DR image data for providing a DR image (present image) (Step 210); and transmitting the converted DR image data to the image data server 109 (Step 211). After receiving the DR image data from the X-ray imaging system 114, the image data server 109 stores the DR image data in the storage unit 111 (Steps 212 and 213). Here, it is assumed that the DR image data is in the DICOM format generally used in the field of the couch positioning unit 115. However, other image formats may be used. Further, this applies also to the DRR image.

Couch Positioning Operation Unit 118

In order to perform couch positioning operations, the couch positioning operation unit 118 performs the steps of: receiving the DRR image (reference image) and the DR image (present image) from the image data server 109; loading them in the couch positioning processor 121 (Step 215); and storing them in the main storage unit 122 and the storage unit 120 (Step 216). The couch positioning operation unit 118 performs the steps of: displaying the loaded DRR and DR images on the monitor 116 (Step 217); setting calculation points (second calculation points) to characteristic points and markers displayed on the DR image; performing positioning operations by use of positional coordinates of calculation points (first calculation points) displayed on the DRR image and calculation points (second calculation points) set to the DR image (Step 218); transmitting the obtained couch displacement to the couch control unit 123 after completion of positioning operations (Step 219); and, transmitting the DR and DRR images having converted coordinates to the image data server 109 after transmitting the couch displacement to the couch control unit (Step 220). The data server 109 stores the received DR image having converted coordinates in the storage unit 111 (Steps 221 and 222). Details of processing from Step 217 for displaying the image data on the monitor 117 to Step 219 for transmitting the displacement to the couch control unit 123 will be mentioned later.

Details of Each Step

Details of Steps 203, 204, 217, and 218 of FIG. 2 will be explained below with reference to FIG. 3.

Figure 2:
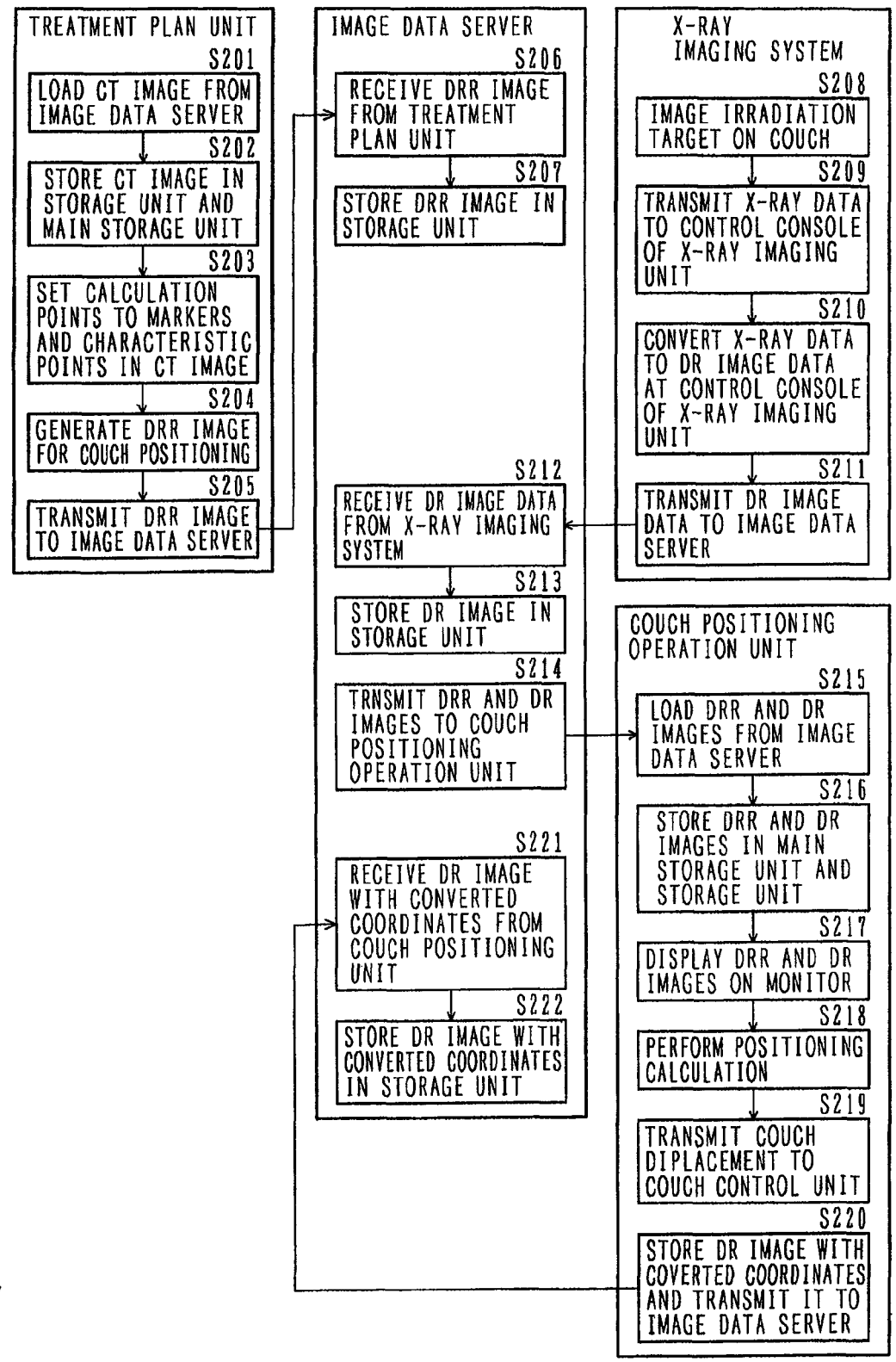
FIG. 2 is a flow chart showing the flow of processing and data in the couch positioning system for radiotherapy according to an embodiment of the present invention.
Figure 3:
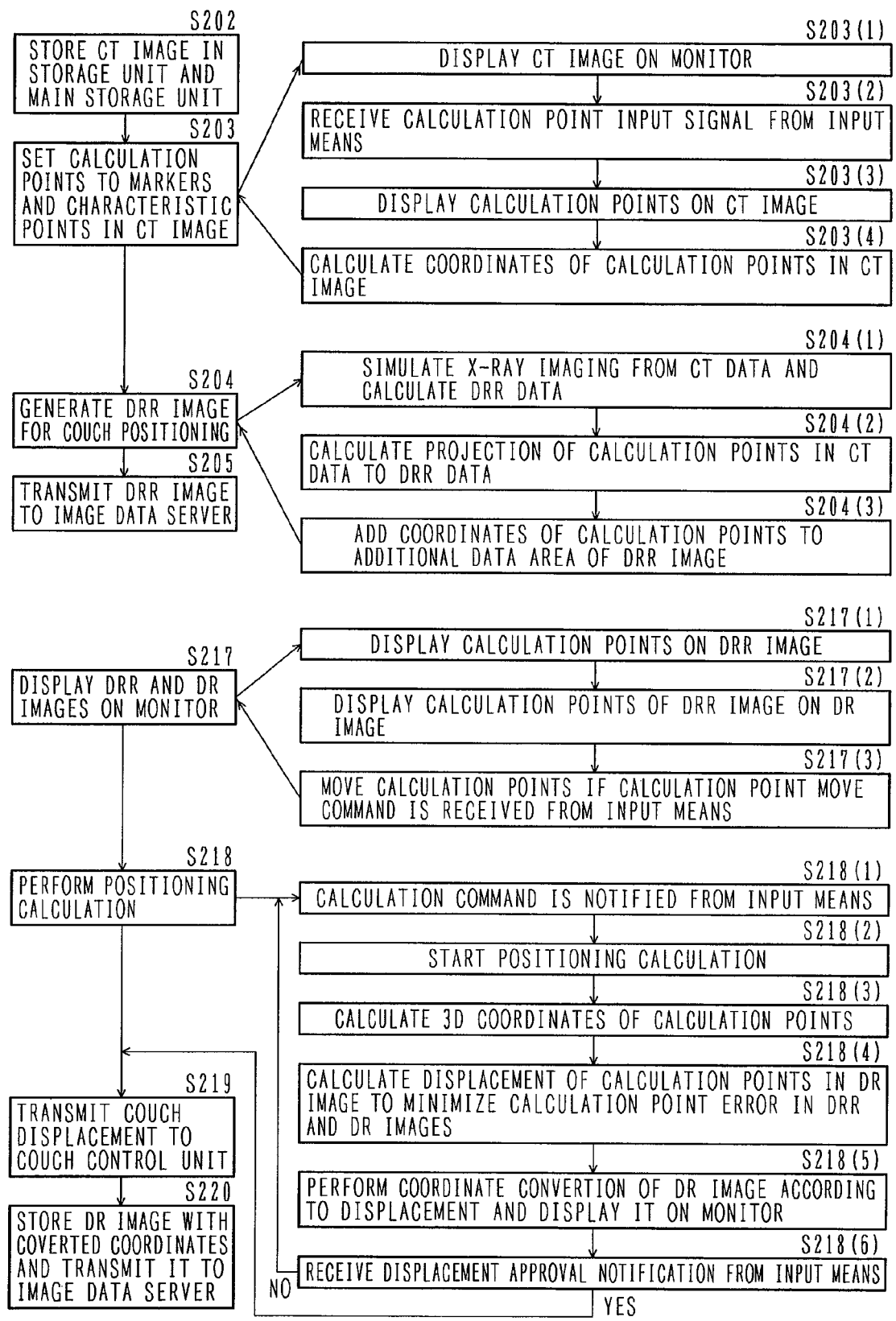
FIG. 3 is a flow chart showing details of Steps 203, 204, 217, and 218 of FIG. 2.

Referring to FIGS. 2 and 3, Step 203 (Steps 203(1) to 203(4)) forms a first operation unit which displays the X-ray CT image on the display unit (monitor 102); and sets calculation points (first calculation points) to the X-ray CT image displayed on the display unit. Step 204 (Step 204(1)) forms a second operation unit which generates first image data for providing a first image (DRR image) that simulates X-ray imaging based on CT image data for providing the X-ray CT image. Step 204 (Steps 204(2) and 204(3)), Step 205, and Step 207 form a third operation unit which performs the steps of: operating the 2D coordinates of the first calculation points in the first image (DRR image) by use of the 3D coordinates of the first calculation points set to the X-ray CT image; adding the 3D and 2D coordinates of the first calculation points to the first image data; and storing the first image data, thus generating a first image file.

Further, referring to FIG. 3, Step 217 (Steps 217(1) to 217(3)) forms a fourth operation unit which performs the steps of: displaying on the display unit (monitor 116) the first image (DRR image) which is a reference image for couch positioning; displaying the first calculation points at positions corresponding to the set first calculation points in the first image; displaying the second image (DR image) which is the present image of the irradiation target on the couch, and setting second calculation points to target positions in the second image (DRR image) displayed on the display unit (monitor 116). Step 218 (Steps 218(1) to 218(6)) forms a fifth operation unit which generates couch positioning data by use of the coordinates of the set first calculation points and the coordinates of the second calculation points.

Further, referring to FIGS. 2 and 3, Steps 220 to 222 form a second image file generator which performs the steps of: generating new second image data reflecting the couch displacement of the couch positioning data and coordinates of new second calculation points; adding the coordinates of the new second calculation points to the new second image data; and storing the new second image data, thus generating a second image file.

Up to DRR Generation (Treatment Plan)

A method of setting 3D coordinates of calculation points to the DRR image will be explained below.

First, a method of setting calculation points in Step 203 will be explained below. The treatment plan unit 101 loads the CT image data, loaded from the image data server and then stored in the storage unit 106, in the main storage unit 108 by use of the treatment plan processor 107 and then displays it on the monitor 102 (Step 203(1)). The CT image is generally composed of a plurality of image files, each being referred to as slice. One specific slice out of a plurality of slices is displayed on the monitor 102. Using the input means 103 (the mouse, the keyboard, etc.), the operator of the treatment plan unit 101 moves the cursor, for example, to a position to be set as a calculation point (first calculation point) on a slice and then specifies that position. The treatment plan operation unit 104 receives a calculation point input signal from the input means 103, and sets a calculation point to the slice (Step 203(2)). If a marker is embedded in the irradiation target before CT imaging, the marker is also reflected on the CT image and therefore the treatment plan operation unit 104 sets calculation points also to the markers reflected on the CT image. Further, the treatment plan operation unit 104 sets calculation points also to corner points of clearly reflected structures such as the backbone, pelvis, or the like. The set calculation points are displayed as on the monitor, being overlapped with the slice of the CT image (Step 203(3)).

Figure 4:
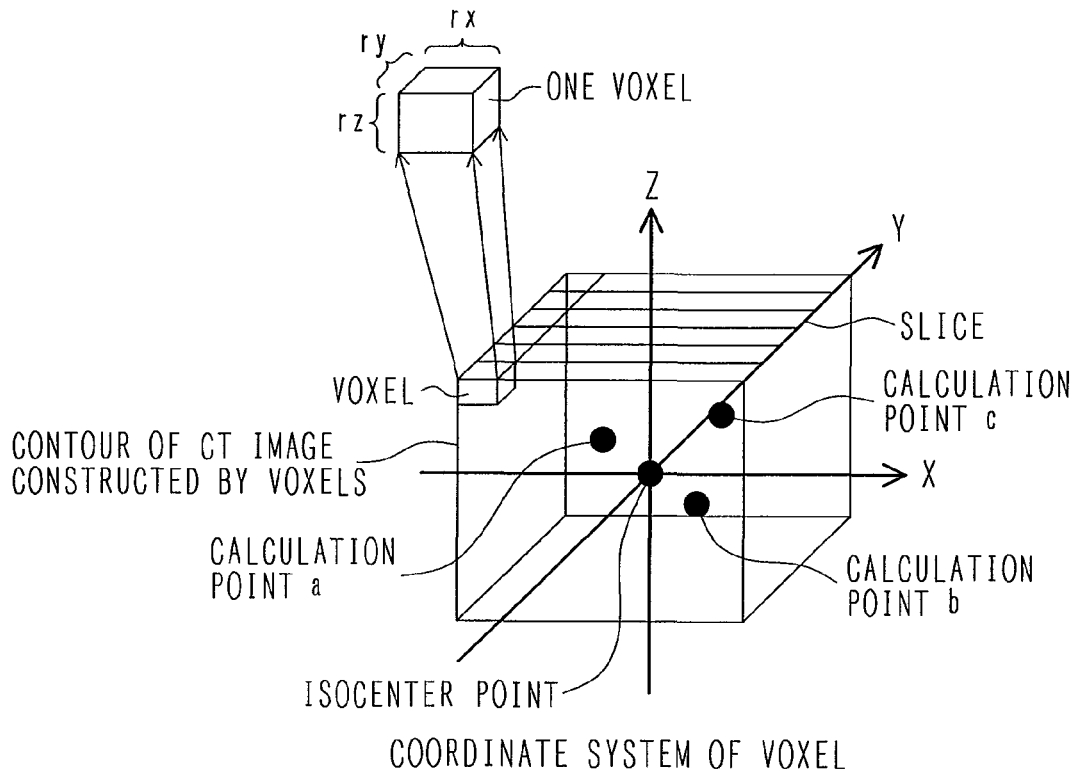
FIG. 4 is a schematic diagram showing 3D data of a CT image as voxel data and a diagram showing a coordinate system set to voxel data used for the present embodiment.

Although the treatment plan unit 101 stores a plurality of CT image slices in the storage unit 106 and the main storage unit 108, these slices are maintained not as a set of 2D sections but as 3D data by the treatment plan processor 107. This 3D data is called a voxel. FIG. 4 is a schematic diagram showing 3D data of a CT image as voxel data and a diagram showing a coordinate system set to voxel data used for the present embodiment. Slices are stacked along the Y-axis direction, and the X and Z axes perpendicularly intersect the Y axis and are in parallel with the slice surface. The X and Z axes perpendicularly intersect with each other. A voxel has size rx in the X-axis direction, size ry in the Y-axis direction, and size rz in the Z-axis direction, as shown in FIG. 4. With the present embodiment, the unit of size is millimeters (mm). Generally, rx and rz are stored in the CT image data file as resolution data. As ry, either a value embedded as a slice thickness in the CT image data file or a slice position stored in the CT image data file is used. ry is obtained by subtracting a slice position of a slice from that of another. These pieces of operational processing are performed by the treatment plan processor 107.

Calculation points set to the slice of the CT image are calculated as 3D coordinates according to the distance from the origin (Step 203(4)) and maintained in the main storage unit 108. Coordinate operations are performed by the treatment plan processor 107. The origin for specifying coordinates of calculation points can be placed anywhere, and freely changed by the operator of the treatment plan unit 101. Generally, in consideration of the convenience at the time of DRR image generation, an isocenter point is used as an origin in many cases. The isocenter point will be set as a slice according to the present embodiment.

Figure 5:
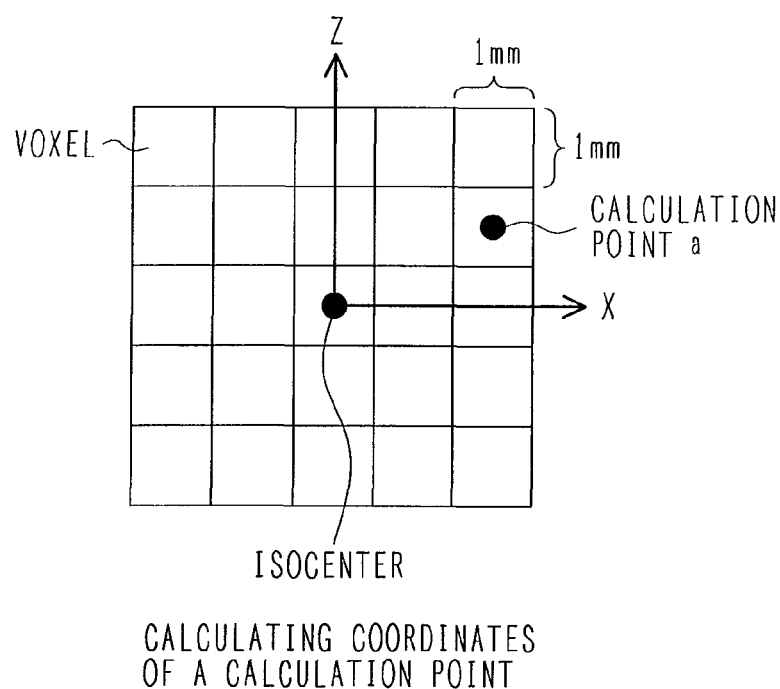
FIG. 5 is a diagram explaining a method of calculating coordinates of a calculation point.

A method of calculating 3D coordinates of a specific calculation point will be explained below. FIG. 5 is a diagram explaining a method of calculating coordinates of a calculation point. Here, the isocenter is used as an origin. Further, a method of calculating X- and Z-coordinates, which are coordinates in the slice, will be explained below to simplify the explanation. The Y-axis coordinate of the calculation point can be calculated by the number of slices from the slice containing the isocenter point to the slice containing the calculation point (referred to as slice index) multiplied by ry. For example, when a calculation point a is positioned as shown in FIG. 5, this calculation point is at two voxels in the positive direction of the X axis and one voxel in the positive direction of the Z axis. Therefore, the coordinates of the calculation point a are (2, 1) when represented with the (X, Z) notation. The unit of coordinates is mm. In FIG. 5, the size of a voxel is 1 mm. Further, supposing that this slice is positioned at two slices in the positive direction of the Y axis from the slice containing the isocenter, the Y-axis coordinate is 2 mm.

One or a plurality of calculation points is set. In order to distinguish between a plurality of set calculation points, each individual calculation point is assigned an independent number, for example, point No. 1, point No. 2, etc. Numbers and coordinates assigned to calculation points are stored in the main storage unit 108. Once a number is specified, the coordinates of a calculation point specified by the number can be obtained.

The isocenter point represents the center of irradiation at the time of radiation irradiation. The treatment plan unit 101 is provided with a function to set an area to be irradiated on the irradiation target. This function is referred to as irradiation area setup and a set area is referred to as an irradiation area. Further, a function to calculate, based on an operator command, how the set irradiation area is to be irradiated from which direction is referred to as an irradiation plan function. Normally, the treatment plan unit 101 sets a gravity center position of the irradiation area and a center position of a circumscription rectangular solid of the irradiation area as an isocenter point. Naturally, the position of the isocenter point can be changed by an operator command. It is an object of couch positioning to match the isocenter point set by the treatment plan unit 101 with the irradiation center at the time of radiation irradiation.

When calculation points have been set to the CT image, the treatment plan unit 101 generates a DRR image for couch positioning. The DRR image is a simulated DR image obtained through computer simulation, and also a simulated X-ray perspective image. The DRR image is generated by operating the X-ray attenuation within the irradiation target by use of the treatment plan operation unit 104 (Step 204(1)). Here, it is known that the X-ray attenuation within the irradiation target can be calculated according to the density distribution thereof. More specifically, the attenuation (within the irradiation target) of the X ray generated by the X-ray source 132 in the X-ray imaging system 114 to irradiate the irradiation target can be calculated by use of a CT value, i.e., CT image data representing the density distribution of the irradiation target. A simulated X-ray called a virtual ray from the X-ray source 132 is allowed to pass through a voxel data element consisting of a plurality of CT slices. The attenuation of the X-ray is calculated in proportion to the distance from the X-ray source 132 and the CT value stored in the voxel data element. Then, the intensity of an attenuated ray at the position of the X-ray image receiver 133 is obtained. At the position of the X-ray image receiver 133, an area in a 2D mesh is formed, for example, with an image size of a 512×512 matrix and a preset resolution. Then, the attenuation of the ray at the center of each element is obtained. By performing such an operation for all the elements on the 2D mesh, it is possible to generate a DRR image at the position of the X-ray image receiver 133. Further, markers embedded in the irradiation target are also reflected on the DRR image.

Generally, as the DRR image for couch positioning, an image is formed by projecting the DRR image (generated at the position of the X-ray image receiver) onto a plane perpendicular to the direction of radiation irradiation (referred to as isocenter plane) on which the isocenter point exists, not the position of the X-ray image receiver. Calculations for projection are performed by use of a ratio of the length of a straight line between the positions of the X-ray source 132 and the X-ray image receiver 133 to the length of a straight line between the positions of the X-ray source 132 and the isocenter plane.

Method of Setting Reference Points to DRR Image

When a DRR image for couch positioning has been generated, the treatment plan unit 101 subsequently performs processing for adding calculation points to the DRR image. Since the calculation points (reference points) inputted in the CT image do not necessarily exist in the CT image as CT values, they are not automatically reflected on the DRR image in the DRR image generation process. Therefore, a location on the DRR image, i.e., the X-ray image receiver 133 where a calculation point having the 3D coordinates is to be projected, and, in the case of projection on the isocenter plane, a location on the isocenter plane where it is positioned are calculated (Step 204(2)). The same method as the method of calculating a DRR image from a CT image is used for operations.

Figure 6:
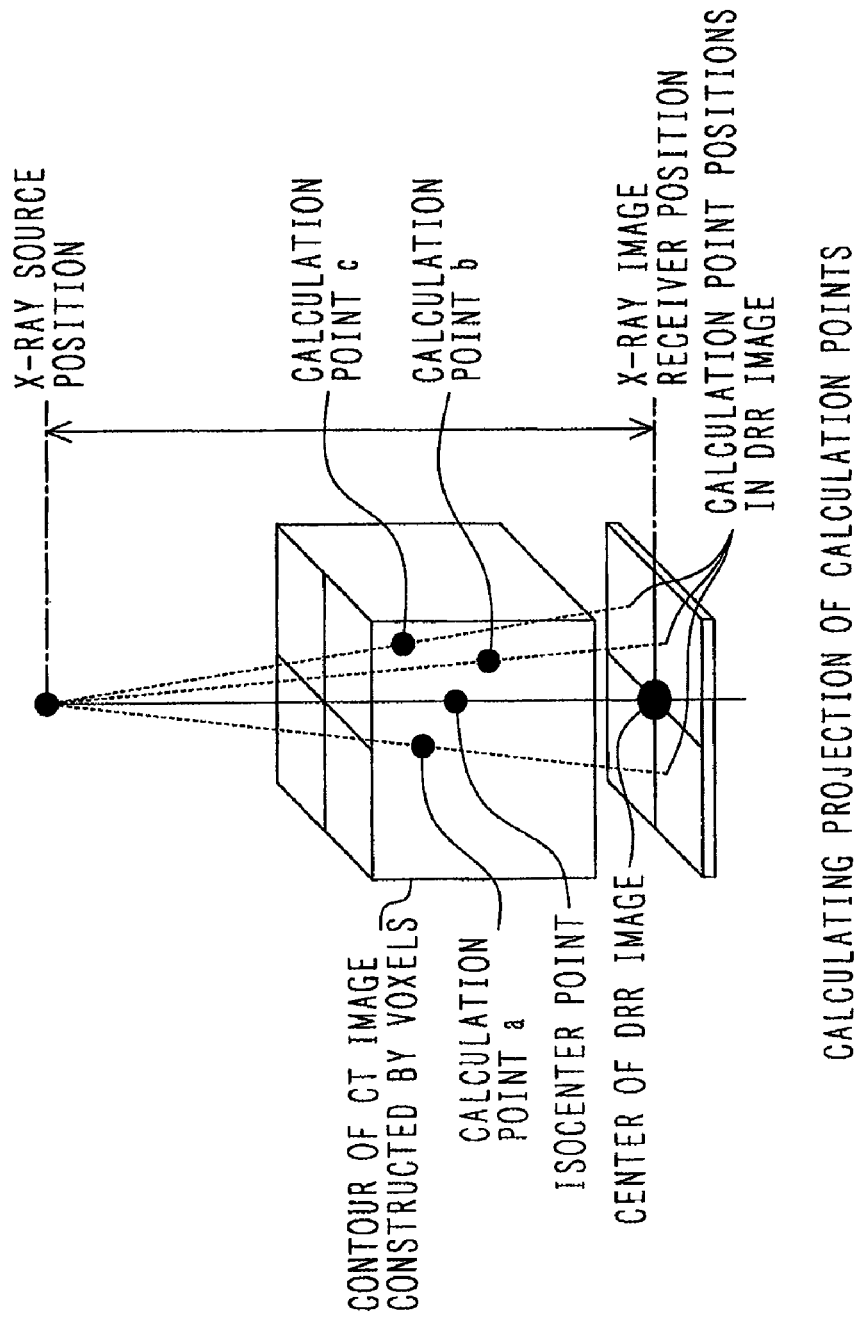
FIG. 6 is a diagram schematically showing a method of calculating projection of 3D calculation points to a DRR image.

FIG. 6 is a schematic diagram of calculation for projection of calculation points to the position of the X-ray image receiver 133. Suppose that calculation points a, b, and c have been set to the CT image data which is composed of voxels, each individual calculation point being assigned a number. In FIG. 6, although the CT image data is actually a set of CT values which is a density distribution of the irradiation target, only a rectangular solid which is the contour of the CT image data is illustrated. Each individual calculation point has 3D coordinates. Straight lines, starting from the position of the X-ray source 132 and passing through the calculation points, intersect with the X-ray image receiver 133. Points at which the straight lines intersect with the X-ray image receiver 133 are used as coordinates of calculation points in the DRR image at the position of the X-ray image receiver. Further, the isocenter point is located at the center of the DRR image, which is also the center of the X-ray image receiver 133. Therefore, also for the coordinates of the calculation points projected on the DRR image, the center of the DRR image to which the isocenter point is projected is used as an origin. If there is a marker at a position having a calculation point setup in the CT image, the marker is also reflected on the DRR image, and the projected calculation point is located on the reflected marker. Further, calculation points in the CT image data and those projected to the DRR image are assigned the same number on a one-to-one basis, making it easier to locate each point. Further, like operations for projection to the isocenter plane in the DRR image, calculation points are also projected to the isocenter plane.

When operations for generating a DRR image are completed, the data format is converted so as to exchange data with another radiation medical apparatus. Usable data formats include the DICOM format widely used, the JPEG image format, etc. In any case, a format having a tag area, a header area, and other additional data areas used to add various data such as pixel values accompanying the image data is used.

Coordinates of calculation points are added to the additional data area together with pixel values of the DRR image (Step 204(3)). In this way, calculation points set by the treatment plan unit 101 can be easily reproduced by use of the couch positioning unit 115. An exemplary configuration of additional data is given below. First, calculation points set to the CT image data are assigned a number by use of the treatment plan processor 107. Each individual calculation point has 3D coordinates (X, Y, Z) following the number. FIG. 7 is a diagram schematically showing the 3D coordinates. In this order, the same processing is repeated the number of times that equals the number of set calculation points. These values are stored in the main storage unit 108. Further, each individual calculation point projected on the DRR image is assigned 2D coordinates. FIG. 8 is a diagram schematically showing the 2D coordinates. The number is common to the 3D and 2D coordinates. Specifying a number makes it possible to search for the 3D coordinates of a calculation point as well as projected 2D coordinates thereof. FIG. 9 is a diagram schematically showing a method of adding data to the DRR image data. The double-line outer frame of FIG. 9 symbolically represents a single DRR image. Each of a number of square boxes represents a unit of data configuration, i.e., an area occupied by the unit data in the main storage unit and the storage unit. Further, symbol < > is a data type identifier which indicates the type of subsequent data. <3D Point> represents a calculation point having 3D coordinates set to the CT image data, and <2D Point> a calculation point having 2D coordinates projected on the DRR image. <Image> means that image data is stored. In addition, the data type identifier includes the identification number of the irradiation target, date of imaging, resolution of the DRR image, matrix size, distance from the X-ray source, etc. which are not shown. Numbers denote the numbers assigned to calculation points. Further, a set of X, Y, Z and X, Y following the number represents the coordinates of the calculation point. Values following <Image> represent pixel values, i.e., DRR image values in this case. Such a DRR image file is created by the treatment plan processor 107, and stored in the main storage unit 108 and as required in the storage unit 106. The generated DRR image file is transmitted to the image data server 109 through the communication unit 105. The image data server 109 stores the received DRR image file in the storage unit 111 (Steps 205 to 207).

Necessity of DRR Images Taken from Two Different Directions

Although generation of a DRR image file has been explained as if only one DRR image file is generated, two or more DRR image files are actually used for couch positioning. That is, DRR images taken from different directions toward the isocenter point are used. By use of two DRR images generated from different directions, it becomes possible to calculate the amount of parallel shift and the amount of rotation around each parallel shift axis (referred to as six degrees of freedom) in 3D space. One DRR image includes 2D data with which only two parallel shifts in the 2D plane and the amount of rotation around the direction perpendicular to the 2D plane can be obtained. Therefore, at least two DRR images are required. A method of operations for actually obtaining six degrees of freedom will be mentioned later. Further, for any DRR image file, the above-mentioned processing for adding the coordinates of calculation points to the DRR image is performed.

Positioning Operations

Figure 10:
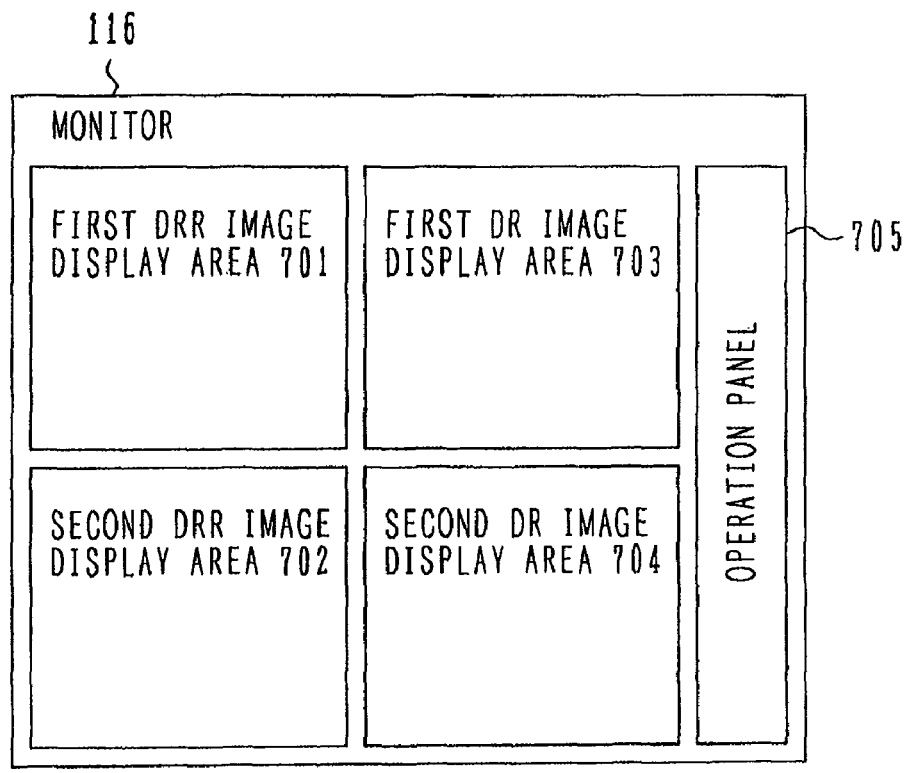
FIG. 10 is a diagram showing an exemplary arrangement of DRR and DR images and operation areas on a monitor of a couch positioning unit.

Operations after Step 217 performed by the couch positioning unit 115 will be explained below. The DRR image (reference image) and the DR image (present image) loaded from the image data server 109 are displayed on the monitor 116, for example, in an arrangement as shown in FIG. 10 (Step 217). This arrangement is referred to as 2×2 display. The couch positioning operation unit is also provided with a method of displaying only a DRR or DR image in two directions and a method of displaying DRR and DR images in a certain direction. Switching between these two display methods is realized by providing a command to the couch positioning processor 121 by use of buttons, comboboxes, and other GUI components displayed on the monitor. In FIG. 10, details of the displayed image are omitted and only an arrangement of image display areas is shown. The monitor 116 includes a first DRR image display area 701 and a second DRR image display area 702 for displaying two DRR images, and a first DR image display area 703 and a second DR image display area 704 for displaying two DR images. Further, the monitor 116 is provided with an operation panel 705 to realize display change, image contrast adjustment, and other operations by means of GUI. Of course, the display areas 701 to 704 and the operation panel 705 of FIG. 10 can be arranged in any desired manner.

Once a DRR image is loaded, images are displayed in the first DRR image display area 701 and the second DRR image display area 702. At the same time, the couch positioning processor 121 calculates coordinates of calculation points (first calculation points or reference points) existing in the additional data area in the image file, and displays them in each display area as a point having a shape of x, □, o, or the like (Step 217(1)). Further, it may be possible to change the color of points according to the calculation point number. For calculation point display in the image display area, the coordinates of <2D Point> embedded in the addition area, i.e., the coordinates of projected calculation points are used. If <2D Point> does not exist in the image file, the couch positioning processor 121 automatically perform calculation based on <3D Point> by use of the distance between the X-ray source 132 and the X-ray image receiver 133, and displays calculation points in the image display area.

When a DR image is displayed on the monitor 116, the couch positioning operation unit 118 displays calculation points (temporary second calculation points) also at coordinate positions in the DR image corresponding to the 2D coordinates of the calculation points added to the DRR image file (Step 217(2)). In this case, the center of the DR image is used as an origin. At the same time, the couch positioning operation unit 118 creates a storage area for the 2D coordinates of calculation points for the DR image also in the main storage unit 122 and stores the 2D coordinates of the calculation points.

Generally, calculation points thus displayed on the DR image deviate from characteristic points and markers set at the time of DRR image generation, because an error occurs when the irradiation target is placed on the couch before radiation irradiation. This is also a reason why couch positioning is required. Therefore, the operator of the couch positioning unit 115 performs editing operations to move calculation points automatically displayed on the DR image by the couch positioning operation unit 118 to the characteristic points or markers. The operator performs editing operations by use of the input means 117, such as the mouse and the keyboard, while checking the calculation points and DR images displayed on the monitor 116 (Step 217(3)). When a calculation point has been moved onto a characteristic point or marker (when positions of the two points are matched), the 2D coordinates of the calculation point (second calculation point) is stored in the storage area. The couch positioning operation unit 118 provides a function to edit calculation points (function to move calculation points) and a function to display and store editing results. It may be possible that a reset function to restore calculation points to initial setup values be included in editing functions.

Upon completion of move and set operations for all calculation points in the DR image, the operator compares them with the DRR image, i.e., data at the time of treatment planning, and provides a command to calculate a deviation of the irradiation target from the irradiation center to the couch positioning operation unit 118. The command is transmitted to the couch positioning processor 121 by use of the input means 117 through the operation panel 705 which is a GUI (Step 218(1)). Upon reception of the relevant signal, the couch positioning processor 121 starts positioning operations (Step 218(2)).

Positioning operations performed by the couch positioning processor 121 will be explained below. The 3D coordinates of calculation points are used for positioning operations. The agreement between the first calculation points in the DRR image and the second calculation points in the DR image means that the following relational expression (Equation 1) is satisfied between calculation points set to the two images.

$$\begin{pmatrix} x\_drr \\ y\_drr \\ z\_drr \\ 1 \end{pmatrix} = M \begin{pmatrix} x\_dr \\ y\_dr \\ z\_dr \\ 1 \end{pmatrix} \quad \text{Eq. 1}$$

M represents a matrix for coordinate conversion. x_DRR, y_DRR, and z_DRR are coordinates of a calculation point in the DRR image; and x_DR, y_DR, and z_DR are coordinates of a calculation point on the corresponding DR image. That is, Equation 1 is satisfied between calculation points assigned the same number. The matrix M includes three parallel shift components and three rotational components, resulting in six degrees of freedom.

$$\begin{pmatrix} c(\phi)c(\theta)-s(\phi)s(\psi)s(\theta) & -c(\psi)s(\theta) & c(\phi)s(\psi)s(\theta)+s(\phi)c(\theta) & \Delta x \\ c(\phi)s(\theta)+s(\phi)s(\psi)c(\theta) & c(\psi)c(\theta) & s(\phi)s(\theta)-c(\phi)s(\psi)c(\theta) & \Delta y \\ -s(\phi)c(\psi) & s(\psi) & c(\phi)c(\psi) & \Delta z \\ 0 & 0 & 0 & 1 \end{pmatrix} \quad \text{Eq. 2}$$

where $\theta$, $\phi$, and $\psi$ denote the amount of rotation; and $\Delta x$, $\Delta y$, and $\Delta z$ the amount of parallel shift. Further, notations s( ) and c( ) represent sin( ) and cos( ), respectively. With couch positioning operations, the amount of rotation and the amount of parallel shift in Equation 2 are obtained so that the relation of Equation 1 is satisfied. These values derive a couch displacement.

Figure 11:
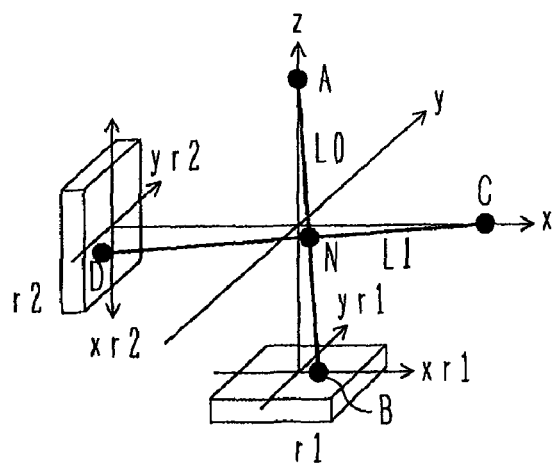
FIG. 11 is a diagram schematically showing a method of reconstructing the 3D coordinates from calculation points having 2D coordinates.

First, it is necessary to calculate 3D coordinates of calculation points on the DR image because calculation points on the DR image have been moved by the operator. Therefore, operations for reconstructing the 3D coordinates from the 2D coordinates of calculation points in the DR image will be performed. FIG. 11 is a diagram schematically showing a method of reconstructing the 3D coordinates from the 2D coordinates in the DR image. r1 is a DR image displayed in the first DR image display area, and r2 is a DR image displayed in the second DR image display area. The x, y, and z axes of FIG. 11 form an orthogonal coordinate system having the present irradiation center as an origin. Further, coordinate axes xr1 and yr1, and xr2 and yr2 are set to the DR images r1 and r2, respectively, having respective centers as an origin. Although actual DR images r1 and r2 are defined as a plane that includes the irradiation center, it is assumed that r1 and r2 are positioned at the positions shown in FIG. 11 on account of the explanation of the operation method. These positions are the same as those for the X-ray image receiver 133. However, the present method is characterized in that the position of the X-ray source 132 and a calculation point in each of the first and second DR images are connected with a straight line, and an intersecting point of the two straight lines or a point having a minimum distance to the two straight lines is obtained. Therefore, the present technique does not care which plane the 2D coordinates are on. Points B and D are calculation points. Further, points A and C represent the position of the X-ray source 132. Further, a straight line which passes through points A and B is referred to as L0, and a straight line which passes through points C and D is referred to as L1. An intersecting point of the two straight lines L0 and L1 or a point having a minimum distance to the two straight lines L0 and L1 is referred to as N.

Ideally, the straight lines L0 and L1 intersect with each other. However, points B and D, which are calculation points set to the DR image, may not be at an intersecting position of the two straight lines because of a move command by the operator. Therefore, a point having a minimum distance to the two straight lines is regarded as the intersecting point N. The straight lines L0 and L1 are represented by parameters s and t as follows:

$$\vec{L_0}(s) = \vec{OA} + s\vec{AB}$$

$$\vec{L_1}(t) = \vec{OC} + t\vec{CD} \quad \text{Eq. 3}$$

where OA denotes a vector from the origin to point A; AB, a vector connecting points A and B; OC, a vector from the origin to point C; and CD, a vector connecting points C and D. An arrow supplied with OA, AB, OC, and CD in the Equation indicates a vector. The distance between the two straight lines, N(s, t), is represented by $$N(s, t) = |\vec{L_0}(s) - \vec{L_1}(t)|^2 \quad \text{Eq. 4}$$

The minimum distance between the two straight lines can be obtained by partially differentiating Equation 4 with respect to s and t. When coefficients of partial differential results are as shown below, $$a \equiv AB_z^2 + AB_y^2 + AB_x^2 \quad \text{Eq. 5}$$
$$b \equiv -AB_zCD_z - AB_yCD_y - AB_xCD_x$$
$$d \equiv CD_z^2 + CD_y^2 + CD_x^2$$
$$e \equiv$$
$$AB_zOC_z + AB_yOC_y + AB_xOC_x - AB_zOA_z - AB_yOA_y - AB_xOA_x$$
$$f \equiv OA_zCD_z + OA_yCD_y + OA_xCD_x -$$
$$CD_zOC_z - CD_yOC_y - CD_xOC_x$$

then, parameters s and t for the minimum distance between the two straight lines can be obtained by the following Equation 6:

$$\binom{s}{t} = \frac{1}{ad - b^2} \binom{de - bf}{-be + af} \quad \text{Eq. 6}$$

The intersecting point N can be obtained by substituting Equation 6 for Equation 4. 3D coordinates of calculation points in the DR image are obtained by such operational processing (Step 218(3)). This operational processing is repeated the number of times that equals the number of calculation points. Further, thus obtained 3D coordinates are stored in the main storage unit 122 by use of the above-mentioned data structure.

When 3D coordinates set to the DR image are obtained in this manner, the couch positioning processor 121 performs processing for obtaining the amount of parallel shift and the amount of rotation shown in Equation 2, which satisfy Equation 1. First, the couch positioning processor 121 calculates an error E between the 3D coordinates of a calculation point set to the DRR image and the 3D coordinates of a calculation point set to the DR image having the same number as the former calculation point. Here, it is assumed that the 3D coordinates of calculation points set to the DR image have been subjected to coordinate conversion using Equation 1. Further, E denotes an error between all calculation points, which is represented by Equation 7.

$$E = \sum_i ((DRR_i(x) - DR_i(x))^2 + \quad \text{Eq. 7}$$
$$(DRR_i(y) - DR_i(y))^2 + (DRR_i(z) - (DR_i(z))^2)$$

where a subscript i denotes a calculation point of the i-th DRR image and the DR image having converted coordinates. Further, the notation DRR( ) means that x, y, and z enclosed in the parentheses are coordinate components.

The couch displacement is obtained by calculating each displacement of Equation 2 so that the error E is minimized (Step 218(4)). Then, this calculation is repeated such that an error E is recalculated. Therefore, an optimization algorithm like the least square means is used to minimize the error E. Then, when the error E has been minimized, the processing for obtaining the couch displacement is completed.

Upon completion of the calculation of the couch displacement, the couch positioning unit 115 performs the steps of: displaying the displacement on the monitor 116 for the operator; converting the coordinates of the DR image based on the displacement; and displaying the DR image having converted coordinates on the screen (Step 218(5)). Coordinate conversion operations are performed by the couch positioning processor 121. Likewise, the couch positioning processor 121 performs coordinate conversion processing also for calculation points inputted and set to the DR image based on the obtained displacement, and displays them on the monitor 116. Then, the couch positioning processor 121 displays a GUI-based dialog for the operator for checking whether the operation results are to be approved. If the operator approves the operation results by use of the input means 117 through the GUI and then the couch positioning processor 121 receives the relevant signal (Step 218(6)), the positioning processor 121 transmits the couch displacement to the couch control unit 123. Further, if the operator transmits a disapproval command to the positioning processor 121 through the GUI, the positioning processor 121 returns to Step 218 and then waits for an operator command.

Storing DR Image

When the couch displacement has been transmitted to the couch and couch positioning has been completed (Step 219), the couch positioning operation unit 118 converts the DR image and calculation points set thereto existing in the main storage unit 122 to a DR image file by use of the couch positioning processor 121, and stores the file in the storage unit 120 (Step 220). The file format is the same as that, for example, of the DRR image file shown in FIG. 9. Further, the DR image has been subjected to coordinate conversion in advance based on the couch displacement, and the calculation point has been likewise subjected to coordinate conversion. Then, the couch positioning operation unit 118 transmits the generated DR image file to the image data server 109 through the communication unit 119. The image data server 109 stores the received DR image file in the storage unit 111 (Steps 220 to 222). An object of the series of processing is to validate the information generated at the time of couch positioning, and to use the DR image instead of the DRR image at the time of couch positioning on and after the following day.

Generally, irradiation to the irradiation target is performed more than once over a plurality of days. Although the use of DRR and DR images at the time of irradiation with the present embodiment has been explained so far, it is also possible to use the above-mentioned DR image (referred to as reference DR image) stored in the image data server 109 instead of the DRR image. Also in this case, the couch positioning operation unit 118 performs the same processing as that performed for the DRR image, to the reference DR image, and then performs couch positioning operations by use of the DR image taken at the time of couch positioning.

In accordance with the above-mentioned present invention, the treatment plan unit 101 performs the steps of: generating calculation points on a CT image; adding the coordinates thereof to a DRR image file to be used for couch positioning as additional information; automatically displaying the calculation points on the monitor 116 when the DRR image is loaded by the couch positioning operation unit 118; and transferring them to the DR image. Therefore, the operator can skip the process of inputting calculation points to the DRR image. It is only necessary for the operator to issue a calculation point correction command to the DR image, making it possible to remarkably simplify the input process of the operator. Further, since all the operator has to do is to issue a calculation point correction command to the DR image, it becomes easier to maintain the couch positioning accuracy, i.e., calculation point accuracy, thereby reducing the couch positioning time.

Further, at the time of second and subsequent couch positioning, the use of the DRR image having calculation point setup or the DR image (reference DR image) of the calculation point stored in the DR image file eliminates the need of inputting calculation points to two different images, and accordingly, the same effects as those obtained at the time of first couch positioning can be obtained. Further, since the operator does not need to input the calculation point to two different images, the reproducibility of input coordinates of the calculation point can be improved further improving the positioning accuracy.

Further, calculation points set to the DR image are also stored as a DR image file after completion of couch positioning, making it easier to validate the couch positioning accuracy and status after couch positioning.

The present invention is not limited to the above-mentioned embodiment. For example, although data files are stored in the image data server 109, it may be possible that the treatment plan unit 101 directly communicates with the couch positioning unit 115 to exchange data files. Further, it may be possible to store DR image files in the storage unit 120 of the couch positioning operation unit 118 without storing them in the image data server 109. Further, the treatment plan unit 101 and the couch positioning operation unit 118 may be integrated into one unit. Further, although the above-mentioned embodiment uses communication of data files, etc. through the network 124, it may be possible to use other storage media, for example, floppy disks, CD-R, and other mass storage media as means for exchanging data files.

Further, in accordance with the embodiment of the present invention, when DR image data is loaded into the couch positioning operation unit 118 at the time of couch positioning, the couch positioning operation unit 118 displays the DR image on the monitor 116 and at the same time automatically copies calculation points set to the DRR image to the DR image; and the operator moves calculation points (second calculation points) to target positions by means of editing functions. However, with the present invention, it may be possible to copy calculation points to the DR image not automatically but through an operator command through the input means 117. Further, the function to copy calculation points to the DR image is not a mandatory function for the present invention. Therefore, it may be possible for the operator to use the input means 117 to input calculation points instead of copying them. However, the use of the function to copy calculation points to the DR image allows the operator to skip the process of displaying them in the DR image, thereby simplifying the input process and reducing the complexity of input operations.

With the embodiment of the present invention, operations to move calculation points set to the DRR image, i.e., editing and change operations, are not explained. However, the operator can perform such editing and change operations at his or her discretion. In this case, the couch positioning operation unit 118 provides the above-mentioned calculation point editing functions also for the DRR image. This function is used if calculation points set by the treatment plan unit 101 are not suitable for conditions of the DR image taken at the time of couch positioning.

Further, in accordance with the present embodiment, the image for couch positioning provided by the treatment plan unit 101 to the couch positioning operation unit 118 is a DRR image. However, in consideration of an object to pass the coordinates of calculation points, it may be possible to transfer CT image data as it is to the couch positioning operation unit 118. In this case, information of calculation point coordinates is added to the CT image file like the case where calculation point coordinates are added to the DRR image.

Further, although the present embodiment is premised on the use of markers or characteristic points within the irradiation target, it may be possible to use both or either one of them. Further, it may also be possible to install jigs at the periphery of the irradiation target for use as markers, or stick seals or the like which do not transmit X-rays on the surface of the irradiation target for use as markers.

The invention claimed is:

1. A couch positioning system for radiotherapy, comprising:
a first image file generator for setting a first calculation point to an X-ray CT image by calculating and storing 3D coordinates of the first calculation point used for couch positioning operations in the X-ray CT image and generating first image data for providing a first image which is a reference image for couch positioning based on CT image data for providing said X-ray CT image; adding the 3D coordinates of the first calculation point to the first image data; and storing the first image data to generate a first image file; and
a couch positioning unit for displaying the first image using the first image file; displaying the first calculation point at a position corresponding to the first calculation point in the first image by use of 2D coordinates acquired from the 3D coordinates of the first calculation point; displaying a second image which is the present image of an irradiation target on the couch; setting a second calculation point used for the couch positioning operations at a target position corresponding to the first calculation point in the second image and performing operations for reconstructing 3D coordinates from the 2D coordinates of the second calculation point; and generating couch positioning data by use of the 3D coordinates of the first calculation point added to the first image data and the 3D coordinates of the second calculation point set to the target position in the second image.

2. The couch positioning system according to claim 1, wherein:
said first image file generator generates, as the first image data, an X-ray perspective image which simulates X-ray imaging based on CT image data for providing the X-ray CT image through operational processing.

3. The couch positioning system according to claim 2, wherein:
said first image file generator performs the steps of:
operating the 2D coordinates of the first calculation point in the first image by use of the 3D coordinates of the first calculation point set to the X-ray CT image; and
adding the 3D coordinates and 2D coordinates as coordinates of the first calculation point to the first image file.

4. The couch positioning system according to claim 1, wherein:
said couch positioning unit uses an X-ray perspective image obtained as the second image by an X-ray imaging system.

5. The couch positioning system according to claim 1, wherein:
said couch positioning unit is provided with an editing function to move a temporary second calculation point set to the second image according to a command of the input means and set the temporary second calculation point having been moved by the editing function as said second calculation point.

6. The couch positioning system according to claim 1, wherein said couch positioning unit is provided with a copy function to display the first calculation point displayed in the first image as a temporary second calculation point at the same coordinate position in the second image, and an editing function to move the temporary second calculation point displayed in the second image according to a command of the input means; and wherein said couch positioning unit sets a temporary second calculation point which has been moved by the editing function as the second calculation point.

7. The couch positioning system according to claim 1, wherein:

said couch positioning unit comprises a second image file generator for generating new second image data reflecting the couch displacement of the couch positioning data and coordinates of a new second calculation point; adding the coordinates of the new second calculation point to the new second image data; and storing the new second image data to generate a second image file.

8. The couch positioning system according to claim 7, wherein:

the second image file generator performs the steps of:
converting the 2D coordinates of the second image and the second calculation point based on couch positioning data generated by the second operation unit; and
storing second image data for providing a second image having converted coordinates and coordinates of a second calculation point as the new second image data and coordinates of the new second calculation point to generate the second image file.

9. The couch positioning system according to claim 1, wherein:

said first image file generator comprises:
a first display unit;
a first operation unit for displaying the X-ray CT image on the first display unit, and setting the first calculation point to the X-ray CT image displayed on the first display unit;
a second operation unit for generating image data which simulates X-ray imaging based on CT image data for providing the X-ray CT image as the first image data; and
a third operation unit for operating the 2D coordinates of the first calculation point in the first image by use of the 3D coordinates of the first calculation point set to the CT image; adding the 3D and 2D coordinates of the first calculation point to the first image data; and storing the first image data to generate a first image file.

10. The couch positioning system according to claim 1, wherein:

said couch positioning unit comprises:
a second display unit;
a fourth operation unit for displaying on the second display unit the first image, the first calculation point, and the second image, and setting the second calculation point to a target position in the second image displayed on the second display unit; and
a fifth operation unit for generating couch positioning data by use of the coordinates of the first calculation point and the coordinates of the second calculation point.

11. A treatment plan unit for radiotherapy, comprising:
a display unit;
a first operation unit for displaying an X-ray CT image on said display unit, and setting a first calculation point to the X-ray CT image displayed on said display unit by calculating and storing 3D coordinates of the first calculation point used for couch positioning operations in the X-ray CT image;
a second operation unit for generating first image data for providing a first image which simulates X-ray imaging based on CT image data for providing the X-ray CT image; and
a third operation unit for operating the 2D coordinates of the first calculation point in the first image by use of the 3D coordinates of the first calculation point set to the X-ray CT image; adding the 3D and 2D coordinates of the first calculation point to the first image data; and storing the first image data to generate a first image file.

12. A couch positioning unit for radiotherapy, comprising:
a display unit;
a storage unit for storing first image data generated based on CT image data for providing said X-ray CT image for providing a first image which is a reference image for couch positioning, the first image data being added with 3D coordinates of a first calculation point used for couch positioning operations and set beforehand in the X-ray CT image;
a fourth operation unit for displaying on said display unit the first image which is the reference image for couch positioning; displaying the first calculation point at a position corresponding to the first calculation point in the first image by use of 2 coordinates acquired from the 3D coordinates of the first calculation point; displaying a second image which is the present image of an irradiation target on the couch; and setting a second calculation point used for the couch positioning operations at a target position corresponding to the first calculation point in the second image; and
a fifth operation unit for performing operations for reconstructing 3D coordinates from the 2D coordinates of the second calculation point; and generating couch positioning data by use of the 3D coordinates of the set first calculation point and the 3D coordinates of the second calculation point.

13. The couch positioning unit according to claim 12, wherein said fourth operation unit is provided with a copy function to display the first calculation point displayed in the first image as a temporary second calculation point at the same coordinate position in the second image, and an editing function to move the temporary second calculation point displayed in the second image according to a command of the input means; and wherein said fourth operation unit sets a temporary second calculation point which has been moved by the editing function as the second calculation point.

14. The couch positioning unit according to claim 12, wherein:

said fifth operation unit performs the steps of:
generating new second image data reflecting the couch displacement of the couch positioning data and coordinates of a new second calculation point;
adding the coordinates of the new second calculation point to the new second image data; and
storing the new second image data, thus generating a second image file.

15. The couch positioning unit according to claim 14, wherein:

said fifth operation unit performs the steps of:

converting the 2D coordinates of the second image and the second calculation point based on couch positioning data generated; and storing second image data for providing a second image having converted coordinates and the coordinates of a second calculation point as the new second image data and the coordinates of the new second calculation point to generate the second image file.

16. The couch positioning unit according to claim 12, wherein:

said fifth operation unit performs the steps of:

operating a deviation between the coordinates of the set first calculation point and the coordinates of the second calculation point;

operating the displacement of the second calculation point with which the deviation is minimized; and generating the couch positioning data based on the displacement.

17. The couch positioning unit according to claim 16, wherein:

said fifth operation unit performs the steps of:

converting the 2D coordinates of the second image and the second calculation point according to the displacement of the second calculation point;

displaying them on said display unit; and validating the couch positioning data when an approval notification is received from the input means.

* * * * *